(12) United States Patent
Tominaga et al.

(10) Patent No.: US 6,485,740 B1
(45) Date of Patent: Nov. 26, 2002

(54) TRANSDERMAL METHOTREXATE PREPARATIONS

(75) Inventors: Kenji Tominaga; Takaaki Hamada, both of Kashima (JP)

(73) Assignee: Yutoku Pharmaceutical Ind., Co., Ltd., Kashima (JP)

(*) Notice: Subject to any disclaimer, the term of this patent is extended or adjusted under 35 U.S.C. 154(b) by 0 days.

(21) Appl. No.: 09/525,747

(22) Filed: Mar. 14, 2000

(51) Int. Cl.[7] ............................ A61F 13/00; A61F 13/02
(52) U.S. Cl. ..................... 424/449; 424/448; 424/443; 514/946; 514/947; 514/825
(58) Field of Search ................. 424/449, 448, 424/443; 514/825, 946, 947

(56) References Cited

U.S. PATENT DOCUMENTS

| | | | | |
|---|---|---|---|---|
| 4,973,576 A | * | 11/1990 | Sakamoto et al. | ............. 514/92 |
| 5,051,260 A | * | 9/1991 | Chess et al. | |
| 5,206,258 A | * | 4/1993 | Doria et al. | ................ 514/403 |
| 5,843,942 A | * | 12/1998 | Breault et al. | ............... 514/247 |
| 5,952,499 A | * | 9/1999 | Whittaker et al. | |
| 5,958,458 A | * | 9/1999 | Norling et al. | |
| 5,961,482 A | * | 10/1999 | Chien et al. | |
| 5,962,516 A | * | 10/1999 | Qi et al. | ..................... 514/468 |
| 5,985,860 A | * | 11/1999 | Toppo | |
| 6,057,122 A | * | 5/2000 | Davidson et al. | .......... 435/68.1 |
| 6,087,336 A | * | 7/2000 | Edward et al. | ............... 514/14 |

FOREIGN PATENT DOCUMENTS

EP  WO 93/07874  *  4/1993

* cited by examiner

*Primary Examiner*—Thurman K. Page
*Assistant Examiner*—Isis Ghali
(74) *Attorney, Agent, or Firm*—Oblon, Spivak, McClelland, Maier & Neustadt, P.C.

(57) ABSTRACT

A methotrexate-containing transdermal preparation effective for rheumatoid arthritis comprises an organic amine. The organic amine may preferably be an alkonolamine such as monoethanolamine, diethanolamine, triethanolamine or diisopropanolamine, or an alkylamine such as ehtylamine, diethylamine or triethylamine. The transdermal preparation is, for example, a plaster, a cataplasm, an ointment, a cream or a lotion.

16 Claims, 3 Drawing Sheets

HAIRLESS MOUSE SKIN PENETRATION TEST (n3)

TRANSDERMAL METHOTREXATE PREPARATIONS

BACKGROUND OF THE INVENTION a) Field of the Invention

This invention relates to percutaneously-applicable preparations (hereinafter called "transdermal preparations") capable of administering methotrexate, which is at present considered to be most effective for rheumatoid arthritis (hereinafter abbreviated as "RA"), more safely than conventional oral preparations while permitting high compliance.

b) Description of the Related Art

As the cause of RA has not been ascertained yet -RA has neither appropriate preventive method nor radical treatment method and is a so-called inveterate disease. RA is a chronic constitutional inflammatory disease and develops characteristic articular lesions. Although RA begins from arthralgia in many cases, its continuation is accompanied by multi-articular destruction or deformity and results in problems of moving functions. It is also often accompanied by extra-articular lesions such as skin, blood vessel, nerve, heart and lung lesions. It is hence a systemic disease lesions of which are not confined to joints. RA patients in Japan are reported to reach as many as 300,000 even on a conservative estimate.

Principal therapeutic drugs for RA at present are non-steroidal anti-inflammatory drugs (NSAIDs) and disease-modifying antirheumatic drugs (DMARDS) and, unless they can provide sufficient effects, immunosuppressants are used.

As first-choice drugs for RA, non-steroidal anti-inflammatory drugs such as salicylic acids, anthranilic acids, phenylacetic acids, indoleacetic acids, propionic acids, pyrazolones, phenacetins, oxycams or solantal type are used.

As second-choice drugs, DMARDs such as gold-containing agents (auranofin, gold sodium thiomalate), SH-containing agents (bucillamine, D-penicillamine), CCAs (disodium lobenzarit) and sulfa drugs (sulfasalazine) are used.

As third-choice drugs, various steroidal drugs are selected.

Further, as fourth-choice drugs, immunosuppressants such as mizoribine, azathioprine, cyclophosphamide, methotrexate and tacrolimus hydrate are used.

Methotrexate that is indicated to be extremely useful among these therapeutic drugs. This drug is indicated that, even when administered at low dosage level against RA, anti-inflammatory effects can be observed from a relatively early stage and remission may be maintained over an extended time. It is usually to RA patients at a dosage of from 2.5 to 7.5 mg/week.

Incidentally, methotrexate is classified as first-choice for RA in Europe and America.

Methotrexate is a metabolic antagonist which was initially developed as therapeutic drug for malignant tumors. For the first time in 1951, it was used for RA and was reported to have effectiveness. It was approved as therapeutic drug for RA in the United States (as early as 1988). Since then, it has been approved as therapeutic drug of RA in 17 countries outside Japan. In Japan, however, it was as late as in 1999 that the application of the national health insurance to methotrexate as a therapeutic drug for RA was approved, although it had already been widely used in clinical fields under the discretion of attending physicians.

Nonetheless, methotrexate is well known to induce various problems such as leukopenia and thrombocytopenia, hepatic problems, gastrointestinal ulcer, diarrhea, mucosal erosion, erythema and alopecia. Development of serious side effects such as bone marrow failure and interstitial pneumonia his arisen as an especially serious problem.

Administration of this drug to patients has conventionally been performed orally, for example, in the form of tablets or capsules. preparation is, however, accompanied by the problem of the first-pass effect at the liver in that upon passage through the liver, a drug is substantially metabolized there before it reaches an affected part. Further, methotrexate has a potential problem of development of side effects as mentioned above although its drug efficacy is strong. For its use, an utmost care is therefore needed. Under these circumstances, methotrexate is used only when an advantage which would be available from its administration is judged to surpass the risk of development of side effects.

If a transdermal preparation which would permit absorption of this drug into blood can be developed, it would then become possible to avoid the first-pass effect at the liver, which is unavoidable for oral preparations, and moreover, to avoid side effects such as gastrointestinal problems. In particular, plasters have some additional advantages. For example, control of percutaneous absorption of the drug makes it possible to maintain its blood at a constant level an extended time and further, to prevent side effects which would otherwise occur due to rapid absorption of the drug in a short time as is observed in the case of oral administration. On top of these, if any problem should arise, simple removal of the preparation makes it possible to immediately stop the supply of the drug, and further, it is also possible to obviate the potential problem of forgetting to give a dose or to give a dose twice. Methotrexate, however, has a high molecular weight and high polarity, so that its percutaneous absorption for transdermal preparations is poor. Therefore, no preparation of the percutaneous absorption type has been disclosed yet for the absorption of the drug into blood.

Incidentally, methotrexate has been confirmed to have therapeutic effect for psoriasis, and its topical preparation has been disclosed (JP 63-27432 A). This topical preparation is, however, effective only to an affected topical part to which the drug is applied, and no additional absorption can be achieved (namely, a topical treatment is intended). On the other hand, JP 55-149212 A states the incorporation of methotrexate in a particular water-insoluble hydrophilic polymer makes it possible to control the velocity of dissolution of the drug by relying upon its water content, and discloses a sustained release preparation useful as a villous tumor therapeutic agent for topical administration to the uterine cavity. However, this sustained release preparation is likewise not intended to achieve absorption of the drug into blood, so that absorption of the drug to the whole body has not been achieved yet.

Presently-available external preparations are intended primarily to give topical effects and under the current circumstances, are physically unable to exhibit the therapeutic effect of methotrexate where inflamed lesions spread at many sites as in RA. If it becomes possible to make the drug reach an effective concentration at the whole body level, its clinical usefulness will be assured. In particular, more people are expected to suffer from deteriorated kidney or liver function as the aging of population in the society advances. Here too, the merits of transdermal preparations are believed to be enjoyed.

SUMMARY OF THE INVENTION

To solve the above-described drawbacks of the conventional oral preparations of methotrexate, the present invention has as a theme thereof the completion of a technique for the delivery of methotrexate into blood, which has heretofore remained as a problem upon formulation of methotrexate into transdermal preparations, and as an object thereof the provision of a transdermal methotrexate preparation effective for RA.

As a result of extensive research on transdermal preparations, the present inventors have found that inclusion of an organic amine along with methotrexate in a base for an external preparation makes it possible to achieve delivery of methotrexate into blood although this delivery has heretofore been difficult.

The present inventors have also found that in an external preparation added with methotrexate, addition of an organic amine in a base leads to a significant improvement in the absorption of methotrexate as an active ingredient.

These findings have led to the completion of the present invention. In one aspect of the present invention, there is accordingly provided a methotrexate-containing transdermal preparation effective for rheumatoid arthritis, which comprises an organic amine.

The methotrexate-containing transdermal preparation according to the present invention can deliver methotrexate, which is now considered to be most effective for RA, into blood more safely than conventional oral preparations while permitting high compliance.

DETAILED DESCRIPTION OF THE INVENTION

Usable examples of the organic amine can include alkylamines such as diethylamine and triethylamine; alkanolamines such as monoethanolamine, diethanolamine, triethanolamine, diisopropanolamine and triisopropanolamine; ethylenediamine; and triethanolamine hydrochloride.

For the transdermal preparation according to the present invention, preparation forms such ointments, creams, lotions, gels and plasters can be used. In view of the object of the preparation that the active ingredient is absorbed into blood and also from the standpoint of controllability on the amount of the active ingredient to be absorbed and handling, a plaster is a more preferable preparation form.

Illustrative of base components to be added to ointments, creams and lotions are bases, emulsifiers, and preservatives. Examples of the bases can include hydrocarbons such as white petrolatum and liquid paraffin; oils and fats, such as soybean oil; waxes such as beeswax and lanolin; fatty acids such as stearic acid and oleic acid; higher alcohols, such as lanolin alcohol and cetostearyl alcohol, and their esters; and macrogols. Examples of the emulsifiers can include nonionic surfactants. Examples of the preservatives can include thymol, methyl pharahydroxybenzoate, and propyl paraoxybenzoate.

As base components which can be added to cataplasms out of plasters, thickeners, humectants, fillers, crosslinking agents, solubilizers, emulsifiers and the like may be mentioned. Specific examples can include: as thickening agents, sodium alginate, gelatin, methylcellulose, carboxyvinyl polymer and poly(sodium acrylate); as humectants, glycerin and macrogols; as fillers, kaolin, titanium dioxide and zinc white; as crosslinking agents, acetaldehyde, dimethyl ketone and aluminum sulfate; as solubilizers, alcohols such as ethanol and 2-propanol, and macrogols; and as emulsifiers, anionic surfactants and nonionic surfactants.

In plasters, rubber-base elastomers, acrylic adhesives and the like are usable as adhesive bases. Specific examples of the rubber-base elastomers can include natural rubber, isoprene rubber, styrene-butadiene rubber (SBR), styrene-isoprene-styrene block copolymer (SIS), styrene-butadiene-styrene block copolymer (SBS), butyl rubber, and polyisobutylene. On the other hand, specific examples of the acrylic adhesives can include alkyl (meth)acrylate (co) polymers, polyacrylate esters, and polymethacrylate esters.

The above-exemplified rubber-base elastomers may be preconditioned by impregnating them with plasticizers such as liquid paraffin and then kneading the thus-obtained masses with tackifier resins, fillers and the like.

Methotrexate in each transdermal preparation according to the present invention may preferably be in such a proportion that, when the preparation is applied to the skin, the active ingredient can be absorbed without any substantial waste while assuring good drug efficacy. The proportion of methotrexate may range from 0.1 to 10 wt. %, preferably from 1 to 5 wt. %.

The present invention will next be describe more specifically by examples. It should however be borne in mind that the present invention is by no means limited to the examples.

EXAMPLES 1–6 & COMPARATIVE EXAMPLES 1–3

Plasters

Based on the formulations shown in Table 1, plasters were prepared as will be described hereinafter.

In each of Examples 1–6, the corresponding organic amine was dissolved in ethanol, and to the resulting solution, methotrexate was added, followed by mixing. The thus-obtained mixture was mixed with a solution of the corresponding base components (rubber-base elastomers or tackifier resin, and known plasticizer, etc.) in toluene. The resulting adhesive mass was casted on a release sheet and then dried. A polyvinyl chloride backing was applied to a surface of the adhesive mass, whereby the plaster was obtained. The plaster of Comparative Example 1 was prepared in a similar manner as in Example 1 except that diisopropanolamine was not added and instead, the proportion of liquid paraffin was increased from 30.0 wt. % to 35.0 wt. %. The plasters of Comparative Examples 2 and 3 were prepared likewise based on their corresponding formulations shown in Table 1.

TABLE 1

Plasters

| | Ex. 1 | Ex. 2 | Ex. 3 | Ex. 4 | Ex. 5 | Ex. 6 | Comp. Ex. 1 | Comp. Ex. 2 | Comp. Ex. 3 |
|---|---|---|---|---|---|---|---|---|---|
| SIS | 27.0 | | | | 27.0 | 27.0 | 27.0 | | |
| Natural rubber | | 30.0 | | 27.0 | | | | | 32.0 |
| Acrylic adhesive | | | 92.0 | | | | | 97.0 | |
| Liquid paraffin | 30.0 | 30.0 | | 32.0 | 33.0 | 28.0 | 35.0 | | 29.0 |
| Ester gum | 35.0 | 33.0 | | 35.0 | 35.0 | 37.0 | 35.0 | | 36.0 |
| Diisopropanolamine | 5.0 | | | | | | | | |
| Monoethanolamine | | 4.0 | 5.0 | | 2.0 | | | | |
| Triethanolamine | | | | 5.0 | | | 5.0 | | |
| Methotrexate | 3.0 | 3.0 | 3.0 | 1.0 | 3.0 | 3.0 | 3.0 | 3.0 | 3.0 |
| Total | 100.0 | 100.0 | 100.0 | 100.0 | 100.0 | 100.0 | 100.0 | 100.0 | 100.0 |

EXAMPLE 7 & COMPARATIVE EXAMPLE 4

Cataplasms

Based on the formulations shown in Table 2, cataplasms of Example 7 & Comparative Example 4 were prepared as will be described hereinafter.

Diisopropanolamine and methotrexate were mixed with a portion of purified water. The resulting aqueous mixture was mixed with an aqueous solution of the corresponding base components [poly(sodiumacrylate), gelatin and glycerin] in the remaining portion of the purified water. After the thus-obtained mass was casted on a release sheet, a nonwoven fabric backing was applied to a surface of the mass, whereby the cataplasm of Example 7 was obtained. The cataplasm of Comparative Example 4 was prepared in a similar manner as in Example 7 except that diisopropanolamine was not used.

TABLE 2

Cataplasms

| | Example 7 | Comparative Example 4 |
|---|---|---|
| Poly(sodium acrylate) | 10.0 | 10.0 |
| Gelatin | 10.0 | 10.0 |
| Glycerin | 30.0 | 30.0 |
| Purified water | Sufficient to produce 100.0 | Sufficient to produce 100.0 |
| Diisopropanolamine | 5.0 | — |
| Methotrexate | 3.0 | 3.0 |
| Total | 100.0 | 100.0 |

EXAMPLE 8 & COMPARATIVE EXAMPLE 5

Ointments

Based on the formulations shown in Table 3, ointments of Example 8 & Comparative Example 5 were prepared as will be described hereinafter.

Diisopropanolamine and methotrexate were mixed with an stirred with gelated hydrocarbon gel whereby the ointment of Example 8 was obtained. The ointment of Comparative Example 5 was prepared in a similar manner as in Example 8 except that diisopropanolamine was not used.

TABLE 3

Ointments

| | Example 8 | Comparative Example 5 |
|---|---|---|
| Hydrocarbon gel | 92.0 | 97.0 |
| Diisopropanolamine | 5.0 | — |
| Methotrexate | 3.0 | 3.0 |
| Total | 100.0 | 100.0 |

EXAMPLE 9 & COMPARATIVE EXAMPLE 6

Creams

Based on the formulations shown in Table 4, creams of Example 9 & Comparative Example 6 were prepared as will be described hereinafter.

Diisopropanolamine and methotrexate were mixed with a portion of purified water. The resulting aqueous mixture was mixed under heat with a liquid mixture of stearic acid, behenyl alcohol, squalane, polyethylene glycol stearate glyceryl monostearate acid and butyl parahydroxybenzoate and also with an aqueous mixture of methyl parahydroxybenzoate, 1,3-butylene glycol and the remaining portion of the purified water. The resulting mass was cooled, whereby the cream of Example 9 was obtained. The cream of Comparative Example 6 was prepared in a similar manner as in Example 9 except that diisopropanolamine was not used.

TABLE 4

Creams

| | Example 9 | Comp. Ex. 6 |
|---|---|---|
| Stearic acid | 7.0 | 7.0 |
| Behenyl alcohol | 0.5 | 0.5 |
| Squalane | 7.0 | 7.0 |
| Polyethylene glycol monostearate | 2.0 | 2.0 |
| Glyceryl monostearate (self-emulsifiable type) | 5.0 | 5.0 |
| Butyl hydroxybenzoate | 0.1 | 0.1 |
| Methyl hydroxybenzoate | 0.1 | 0.1 |
| 1,3-butylene glycol | 5.0 | 5.0 |
| Purified water | Sufficient to produce 100.0 | Sufficient to produce 100.0 |
| Diisopropanolamine | 5.0 | — |
| Methotrexate | 3.0 | 3.0 |
| Total | 100.0 | 100.0 |

EXAMPLE 10 & COMPARATIVE EXAMPLE 7

Lotions

Based on the formulations shown in Table 5, lotions of Example 10 & Comparative Example 7 were prepared as will be described hereinafter.

Diisopropanolamine and methotrexate were mixed with a portion of purified water. The resulting aqueous mixture was mixed under heat with a liquid mixture of stearic acid, behenyl alcohol, polyoxyethylene sorbitan monostearate, glyceryl monostearate and butyl parahydroxybenzoate and also with an aqueous mixture of methyl parahydroxybenzoate, 1,3-butylene glycol and another portion of the purified water. The resulting mixture was cooled. After that, the thus-cooled mixture was mixed with a water-base dispersion of carboxyvinyl polymer in the remaining water, whereby the lotion of Example 10 was obtained. The lotion of Comparative Example 7 was prepared in a similar manner as in Example 10 except that diisopropanolamine was not used.

TABLE 5

Lotions

|  | Example 10 | Comp. Ex. 7 |
| --- | --- | --- |
| Stearic acid | 1.0 | 1.0 |
| Behenyl alcohol | 0.5 | 0.5 |
| Polyoxyethylene sorbitan monostearate | 1.0 | 1.0 |
| Glyceryl monostearate (self-emulsifiable type) | 1.0 | 1.0 |
| Butyl hydroxybenzoate | 0.1 | 0.1 |
| Methyl hydroxybenzoate | 0.1 | 0.1 |
| Carboxyvinyl polymer | 1.0 | 1.0 |
| 1,3-butylene glycol | 5.0 | 5.0 |
| Purified water | Sufficient to produce 100.0 | Sufficient to produce 100.0 |
| Diisopropanolamine | 5.0 | — |
| Methotrexate | 3.0 | 3.0 |
| Total | 100.0 | 100.0 |

Test 1 (Skin Penetration Test)

Using excised dorsal skins of hairless mice, a skin permeation cell was conducted to compare skin penetration properties of methotrexate in the preparations of some of the invention examples.

The preparations were applied to the excised dorsal skins of the hairless mice, respectively. Each excised dorsal skin with its corresponding preparation applied thereon was attached to an in vitro membrane penetration tester. Using a phosphate buffer of pH 7.4 as a receptor solution, an amount of methotrexate migrated into the receptor solution was measured at predetermined intervals cut off by a hair clipper. The results of measurements on the plasters of Examples 1–3 and 7 and Comparative Examples 1 and 2 are plotted in FIG. 1.

Figure 1:
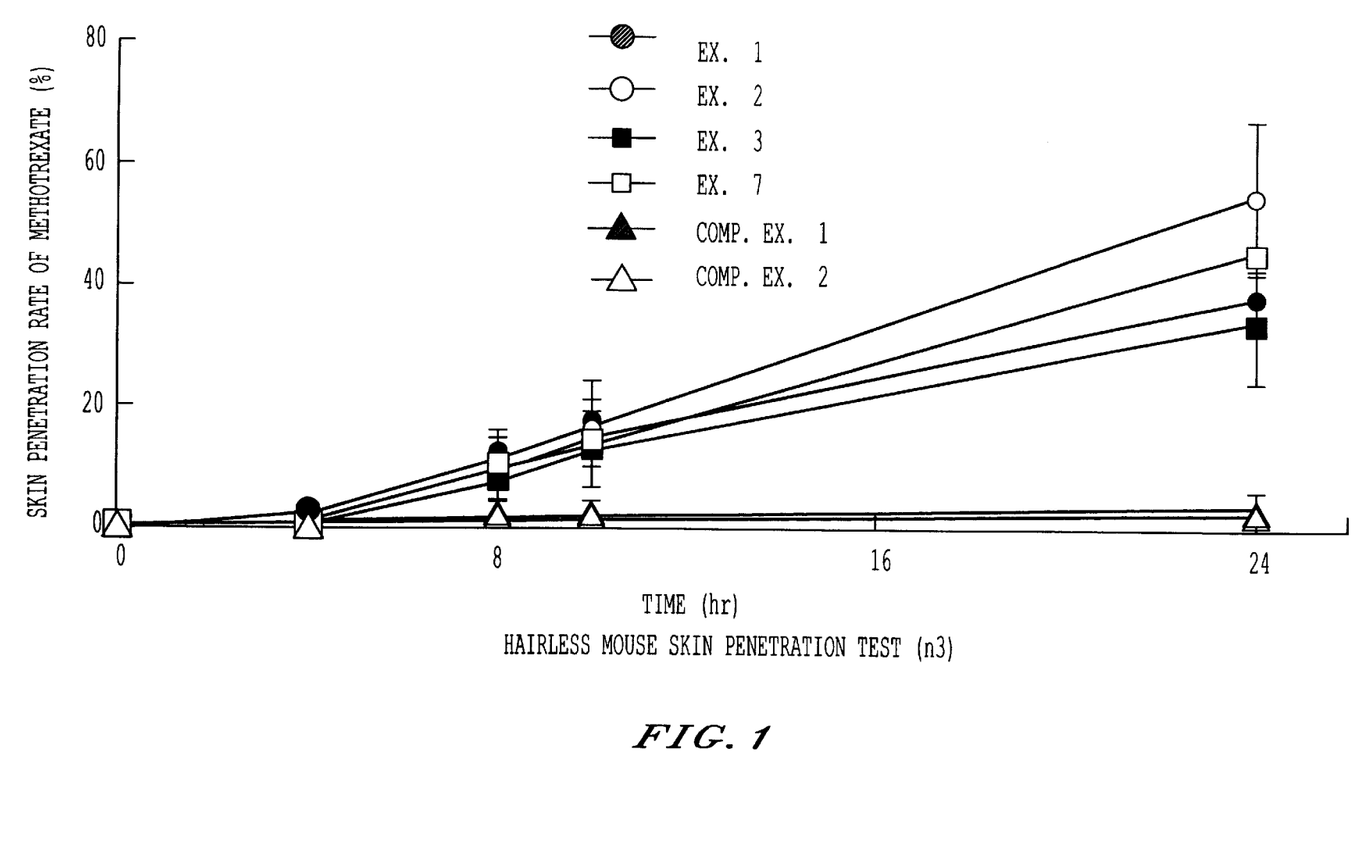
FIG. 1 is a graph showing skin penetration properties of plasters of Examples 1–3 and 7 and Comparative Examples 1,2 as determined by a hairless mouse skin penetration test.

As is evident from FIG. 1, the plasters of Examples 1–3 and 7, in each of which the corresponding organic amine was added, showed higher skin penetration property than the plasters of Comparative Examples 1 and 2 in each of which no organic amine was not added. Incidentally, skin penetration property was also investigated with respect to the ointment of Example 8, the cream of Example 9, the ointment of Comparative Example 5, the cream of Comparative Example 6 and the lotion of Comparative Example 7. The preparations according to the present invention, which were added with the organic amine, similarly exhibited higher skin penetration property than that or the preparations of the comparative examples.

Test 2 (Percutaneous Absorption Test)

Rats (Wistar strain, 7 weeks old, male, 200 g to 250 g) were cut off by a hair clipper at dorsal skins, to which the plasters (4 $cm^2$) of Example 1 and Comparative Example 1 were then applied, respectively. After the initiation of the test, blood samples were collected at predetermined constant intervals to measure blood concentrations of methotrexate. Further, the plasters were peeled off 48 hours later, and the blood concentrations of methotrexate were tracked until 54 hours later. The results are plotted in FIG. 2.

Figure 2:
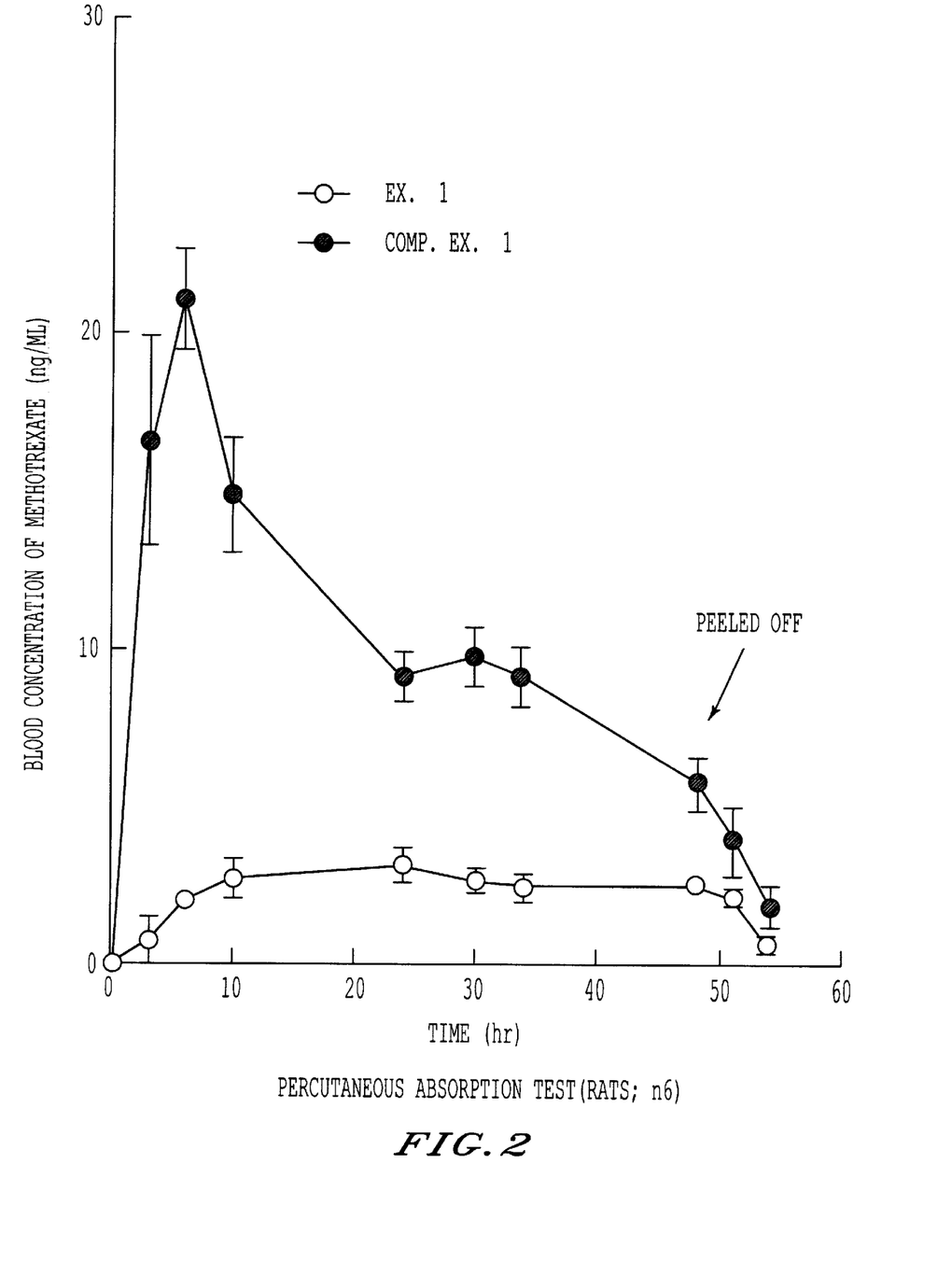
FIG. 2 is a graph depicting changes in the blood concentration of methotrexate with time when the plasters of Example 1 and Comparative Example 1 were applied to rats.

As is apparent from FIG. 2, the plaster of Example 1 in which the organic amine was added showed higher percutaneous absorption property and also, longer maintenance of blood concentration than those of the plaster of Comparative Example 1 in which no organic amine was added. Moreover, even in the case of the plaster of Example 1, the blood concentration of methotrexate promptly decreased after the removal of the plaster.

Test 3 (Drug Efficacy Test)

Swelling inhibitory effects for arthritis, which were induced by an adjuvant in rats employed as RA models, were tested.

Rats (Lewis strain, 7 weeks old, male, 200 g to 250 g) were depilated at dorsal skins, to which the plasters (4 $cm^2$) of Example 1 and Comparative Example 1 were then applied, respectively. Arthritis was thereafter induced by the adjuvant, and paw edema volumes were measured along the passage of time to evaluate drug efficacy. The measurement results are plotted along with the results of a measurement on a control (non-treated) in FIG. 3.

Figure 3:
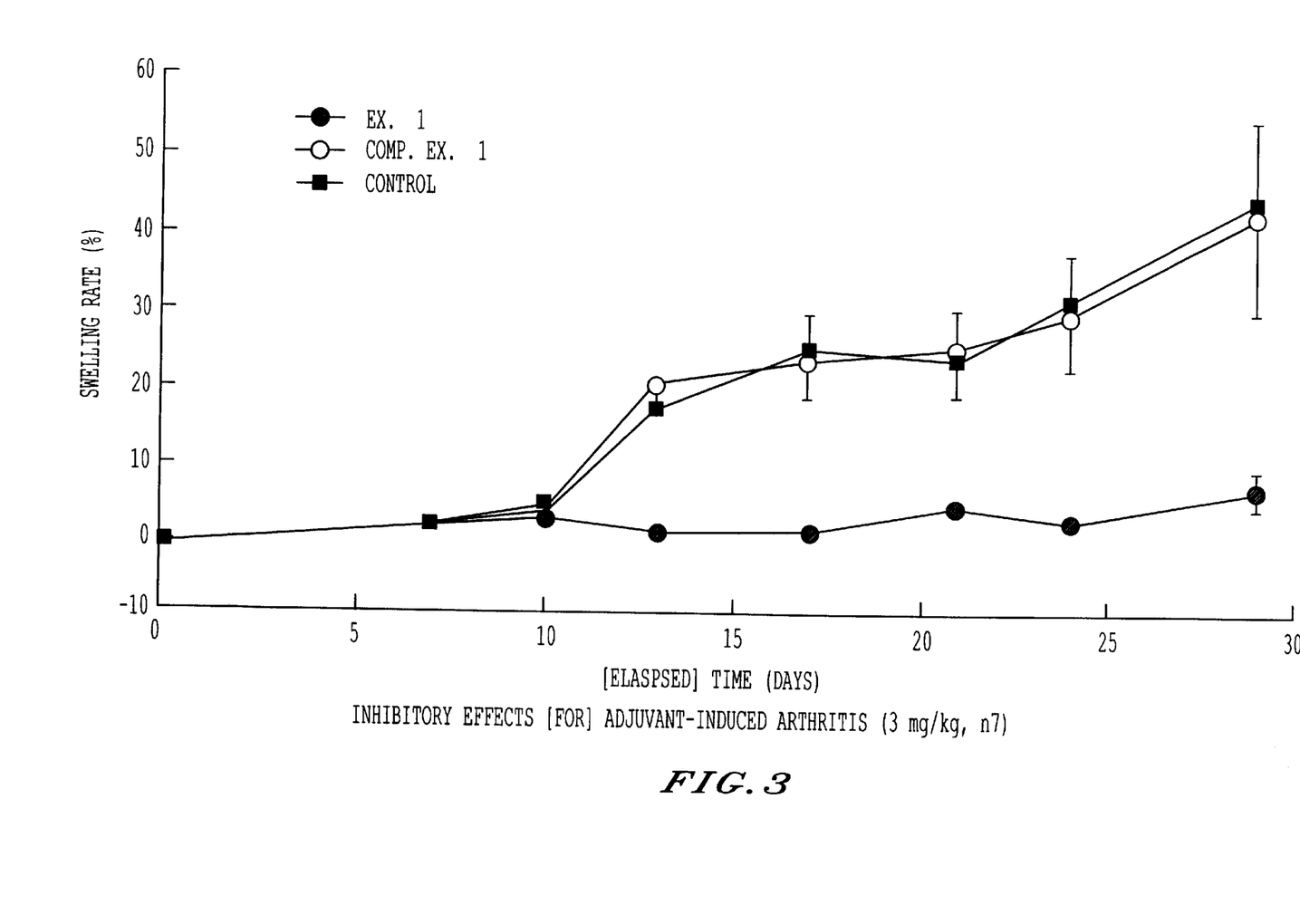
FIG. 3 is a graph illustrating changes in the swelling rates of arthritis induced by an adjuvant in rats applied with the plasters of Example 1 and Comparative Example 1.

As is clearly envisaged from FIG. 3, the plaster of Example 1 in which the organic amine was added showed stronger edema inhibitory effects than those of the plaster of Comparative Example in which no organic amine was added. As a matter of fact, no difference was observed whatsoever between the plaster of Comparative Example and the control (non-treated).

What is claimed is:

1. A method for delivering methotrexate into the blood comprising:
    transdermally administering to a subject in need of treatment a composition comprising:
        methotrexate and at least 2 wt. % of an alkylamine or an alkanolamine selected from the group consisting of ethylamine, diethylamine, triethylamine, monoethanolamine, diethanolamine, triethanolamine and diisopropanolamine.

2. The method of claim 1, wherein said subject has rheumatoid arthritis.

3. The method of claim 1, wherein said composition comprises ethylamine, diethylamine or triethylamine.

4. The method of claim 1, wherein said composition comprises monoethanolamine, diethanolamine, triethanolamine or diisopropanolamine.

5. A product or preparation that delivers methotrexate transdermally into the blood, comprising:
    methotrexate and
    at least 2 wt. % of an alkylamine or an alkanolamine selected from the group consisting of ethylamine, diethylamine, triethylamine, monoethanolamine, diethanolamine, triethanolamine, and diisopropanolamine.

6. The product or preparation of claim 5, which comprises a plaster, a cataplasm, an elastomers, an adhesive or an adhesive sheet.

7. The product or preparation of claim 5, wherein the proportion of methotrexate ranges from about 0.1 to 10 wt. %.

8. A rubber-based elastomer or acrylic adhesive comprising:

methotrexate and at least 2 wt. % of an alkylamine or an alkanolamine selected from the group consisting of ethylaamine, diethylamine, triethylamine, monoethanolamine, diethanolamine, triethanolamine and diisopropanolamine.

9. The product or preparation of claim 5 comprising at least 2 wt. % of ethylamine, diethylamine or triethylamine.

10. The product or preparation of claim 5 comprising at least 2 wt. % of monoethanolamine, diethanolamine, or diisopropanolamine.

11. The product or preparation of claim 5 comprising at least 2 wt. % of triethanolamine.

12. A transdermal preparation, comprising:

methotrexate and at least 2 wt. % of an alkylamine or an alkanolamine selected from the group consisting of ethylamine, diethylamine, triethylamine, monoethanolamine, diethanolamine, triethanolamine and diisopropanolamine.

13. The transdermal preparation of claim 12, selected from the group consisting of a plaster, a cataplasm, an ointment, a cream and a lotion.

14. The transdermal preparation of claim 12 comprising at least 2 wt. % of ethylamine, diethylamine or triethylamine.

15. The transdermal preparation of claim 12 comprising at least 2 wt. % of monoethanolamine, diethanolamine, or diisopropanolamine.

16. The transdermal preparation of claim 12 comprising at least 2 wt. % of triethanolamine.

* * * * *

UNITED STATES PATENT AND TRADEMARK OFFICE
CERTIFICATE OF CORRECTION

PATENT NO. : 6,485,740 B1
DATED : November 26, 2002
INVENTOR(S) : Kenji Tominaga et al.

It is certified that error appears in the above-identified patent and that said Letters Patent is hereby corrected as shown below:

Column 1,
Line 31, "(DMARDS)" should read -- DMARDs) --;
Line 47, "that" should be deleted;
Line 52, "is usually to RA" should read -- is usually adminstered to RA --;
Line 54, "as first-choice for" should read -- as first-choice drug for --.

Column 2,
Line 6, "monia his arisen" should read -- monia has arisen --;
Line 9, "capsules. preparation is," should read -- capsules. An oral preparation is --;
Line 25, "its blood at a" should read -- its blood concentration at a --;

Column 3,
Line 64, "pharahydroxybenzoate" should read -- parahydroxybezoate --
Line 64, "paraoxybenzoate." should read -- parahydroxybenzoate. --

Columns 5 and 6,
Table 1,

|  | Ex. 1 | Ex. 2 | Ex. 3 | Plasters Ex. 4 | Ex. 5 | Ex. 6 | Comp. Ex. 1 | Comp. Ex. 2 | Comp. Ex. 3 |
|---|---|---|---|---|---|---|---|---|---|
| SIS | 27.0 |  |  |  | 27.0 | 27.0 | 27.0 |  |  |
| Natural rubber |  | 30.0 |  | 27.0 |  |  |  |  | 32.0 |
| Acrylic adhesive |  |  | 92.0 |  |  |  |  | 97.0 |  |
| Liquid paraffin | 30.0 | 30.0 |  | 32.0 | 33.0 | 28.0 | 35.0 |  | 29.0 |
| Ester gum | 35.0 | 33.0 |  | 35.0 | 35.0 | 37.0 | 35.0 |  | 36.0 |
| Diisopropanolamine | 5.0 |  |  |  |  |  |  |  |  |
| Monoethanolamine |  | 4.0 | 5.0 |  | 2.0 |  |  |  |  |
| Triethanolamine |  |  |  | 5.0 |  |  | 5.0 |  |  |
| Methotrexate | 3.0 | 3.0 | 3.0 | 1.0 | 3.0 | 3.0 | 3.0 | 3.0 | 3.0 |
| Total | 100.0 | 100.0 | 100.0 | 100.0 | 100.0 | 100.0 | 100.0 | 100.0 | 100.0 | should read

|  | Ex. 1 | Ex. 2 | Ex. 3 | Plasters Ex. 4 | Ex. 5 | Ex. 6 | Comp. Ex. 1 | Comp. Ex. 2 | Comp. Ex. 3 |
|---|---|---|---|---|---|---|---|---|---|
| SIS | 27.0 |  |  |  | 27.0 | 27.0 | 27.0 |  |  |
| Natural rubber |  | 30.0 |  | 27.0 |  |  |  |  | 32.0 |
| Acrylic adhesive |  |  | 92.0 |  |  |  |  | 97.0 |  |
| Liquid paraffin | 30.0 | 30.0 |  | 32.0 | 33.0 | 28.0 | 35.0 |  | 29.0 |
| Ester gum | 35.0 | 33.0 |  | 35.0 | 35.0 | 37.0 | 35.0 |  | 36.0 |
| Diisopropanolamine | 5.0 |  |  |  |  |  |  |  |  |
| Monoethanolamine |  | 4.0 | 5.0 |  | 2.0 |  |  |  |  |
| Triethanolamine |  |  |  | 5.0 |  | 5.0 |  |  |  |
| Methotrexate | 3.0 | 3.0 | 3.0 | 1.0 | 3.0 | 3.0 | 3.0 | 3.0 | 3.0 |
| Total | 100.0 | 100.0 | 100.0 | 100.0 | 100.0 | 100.0 | 100.0 | 100.0 | 100.0 |

Line 64, "with gelated hydrocarbon" should read -- with hydrocarbon --.

UNITED STATES PATENT AND TRADEMARK OFFICE
CERTIFICATE OF CORRECTION

PATENT NO. : 6,485,740 B1
DATED : November 26, 2002
INVENTOR(S) : Kenji Tominaga et al.

It is certified that error appears in the above-identified patent and that said Letters Patent is hereby corrected as shown below:

Column 6,
Line 39, "stearate" should read -- stearate, --;
Table 4,

|  | Creams | |
| --- | --- | --- |
|  | Example 9 | Comp. Ex. 6 |
| Stearic acid | 7.0 | 7.0 |
| Behenyl alcohol | 0.5 | 0.5 |
| Squalane | 7.0 | 7.0 |
| Polyethylene glycol monostearate | 2.0 | 2.0 |
| Glyceryl monostearate (self-emulsifiable type) | 5.0 | 5.0 |
| Butyl hydroxybenzoate | 0.1 | 0.1 |
| Methyl hydroxybenzoate | 0.1 | 0.1 |
| 1,3-butylene glycol | 5.0 | 5.0 |
| Purified water | Sufficient to produce 100.0 | Sufficient to produce 100.0 |
| Diisopropanolamine | 5.0 | -- |
| Methotrexate | 3.0 | 3.0 |
| Total | 100.0 | 100.0 | should read

|  | Creams | |
| --- | --- | --- |
|  | Example 9 | Comp. Ex. 6 |
| Stearic acid | 7.0 | 7.0 |
| Behenyl alcohol | 0.5 | 0.5 |
| Squalane | 7.0 | 7.0 |
| Polyethylene glycol monostearate | 2.0 | 2.0 |
| Glyceryl monostearate (self-emulsifiable type) | 5.0 | 5.0 |
| Butyl parahydroxybenzoate | 0.1 | 0.1 |
| Methyl parahydroxybenzoate | 0.1 | 0.1 |
| 1,3-butylene glycol | 5.0 | 5.0 |
| Purified water | Sufficient to produce 100.0 | Sufficient to produce 100.0 |
| Diisopropanolamine | 5.0 | -- |
| Methotrexate | 3.0 | 3.0 |
| Total | 100.0 | 100.0 |

Column 7,
Table 5,

|  | Lotions | |
| --- | --- | --- |
|  | Example 10 | Comp. Ex. 7 |
| Stearic acid | 1.0 | 1.0 |
| Behenyl alcohol | 0.5 | 0.5 |
| Polyoxyethylene sorbitan monostearate | 1.0 | 1.0 |
| Glyceryl monostearate (self-emulsifiable type) | 1.0 | 1.0 |
| Butyl hydroxybenzoate | 0.1 | 0.1 |
| Methyl hydroxybenzoate | 0.1 | 0.1 |
| Carboxyvinyl polymer | 1.0 | 1.0 |
| 1,3-butylene glycol | 5.0 | 5.0 |
| Purified water | Sufficient to produce 100.0 | Sufficient to produce 100.0 |
| Diisopropanolamine | 5.0 | -- |
| Methotrexate | 3.0 | 3.0 |
| Total | 100.0 | 100.0 | should read

|  | Lotions | |
| --- | --- | --- |
|  | Example 10 | Comp. Ex. 7 |
| Stearic acid | 1.0 | 1.0 |
| Behenyl alcohol | 0.5 | 0.5 |
| Polyoxyethylene sorbitan monostearate | 1.0 | 1.0 |
| Glyceryl monostearate (self-emulsifiable type) | 1.0 | 1.0 |
| Butyl parahydroxybenzoate | 0.1 | 0.1 |
| Methyl parahydroxybenzoate | 0.1 | 0.1 |
| Carboxyvinyl polymer | 1.0 | 1.0 |
| 1,3-butylene glycol | 5.0 | 5.0 |
| Purified water | Sufficient to produce 100.0 | Sufficient to produce 100.0 |
| Diisopropanolamine | 5.0 | -- |
| Methotrexate | 3.0 | 3.0 |
| Total | 100.0 | 100.0 |

UNITED STATES PATENT AND TRADEMARK OFFICE
CERTIFICATE OF CORRECTION

PATENT NO. : 6,485,740 B1
DATED : November 26, 2002
INVENTOR(S) : Kenji Tominaga et al.

It is certified that error appears in the above-identified patent and that said Letters Patent is hereby corrected as shown below:

<u>Column 7 cont'd,</u>
Line 47, "a skin permeation cell was" should read -- a skin penetration test was --;
Line 48, "vito membrane penetration tester." should read -- vitro membrane permeation cell. --;
Line 51, "cut off by a hair clipper." should read -- with time. --;
Line 59, "was not added." should read -- was added. --;
Line 66, "than that or the" should read -- than that of the --;

<u>Column 8,</u>
Line 35, "whatsoever between the" should read -- between the --;
Line 63, "an elastomers," should read -- an elastomer, --;

<u>Column 9,</u>
Line 5, "of ethylaamine," should read -- of ethylamine, --.

Signed and Sealed this

Thirtieth Day of September, 2003

JAMES E. ROGAN
*Director of the United States Patent and Trademark Office*